US008703752B2

(12) United States Patent
Ruat et al.

(10) Patent No.: US 8,703,752 B2
(45) Date of Patent: Apr. 22, 2014

(54) USE OF MIFEPRISTONE AND DERIVATIVES THEREFOR AS HEDGEHOG PROTEIN SIGNALING PATHWAY MODULATORS AND APPLICATIONS OF SAME

(75) Inventors: Martial Ruat, Bourg-la-Reine (FR); Elisabeth Traiffort, Paris (FR); Hélène Faure, Gif-sur-Yvette (FR)

(73) Assignee: Centre National de la Recherche Scientifique, Paris Cedex (FR)

( * ) Notice: Subject to any disclaimer, the term of this patent is extended or adjusted under 35 U.S.C. 154(b) by 1423 days.

(21) Appl. No.: 10/543,004

(22) PCT Filed: Jan. 22, 2004

(86) PCT No.: PCT/FR2004/000151
§ 371 (c)(1),
(2), (4) Date: Oct. 11, 2006

(87) PCT Pub. No.: WO2004/067550
PCT Pub. Date: Aug. 12, 2004

(65) Prior Publication Data
US 2007/0060546 A1    Mar. 15, 2007

(30) Foreign Application Priority Data
Jan. 22, 2003 (FR) ...................................... 03 00646

(51) Int. Cl.
*A01N 45/00* (2006.01)
*A01N 57/00* (2006.01)
*A61K 31/56* (2006.01)
*A61K 31/66* (2006.01)

(52) U.S. Cl.
USPC .......................................... 514/171; 514/114

(58) Field of Classification Search
USPC ................................................. 514/171, 114
See application file for complete search history.

(56) References Cited

U.S. PATENT DOCUMENTS

| 4,386,085 A | 5/1983 | Teutsch et al. |
| 5,468,741 A * | 11/1995 | Yen ................................. 514/179 |

FOREIGN PATENT DOCUMENTS

| WO | 98/27986 | 7/1998 |
| WO | 98/48784 | 11/1998 |
| WO | WO 98/48784 | * 11/1998 |
| WO | 99/59596 | 11/1999 |
| WO | 00/24390 | 5/2000 |
| WO | 00/24390 A1 | 5/2000 |

OTHER PUBLICATIONS

Haak et. al., The Lancet (1990) 336:124-125.*
Gettys et. al, (International Journal of Obesity (1997) 21:865-873.*
Haak et. al. (The Lancet (1990) 336:124-125).*
Berman et. al. (Science (2002) 297:1559-1561).*
Tremblay (Expert Opinion in Therapeutic Patents (2009) 19:1039-1056).*
Pinski et. al. (journal of Clinical Endocrinology and metabolism (1993) 77:1388-1392).*
Goodman and Gilman's The Pharmacological Basis of Therapeutics (Tenth Edition (2001), McGraw Hill, pp. 5-6 and 24-29).*
Bastin et. al. (Organic Process Research Development (2000) 4:427-435).*
"Successful mifepristone treatment of recurrent, inoperable meningioma",The Lancet, p. 124-125, vol. 336.
"Mifepristone (RU 486)", R. M. Bonelli, Nr. 6/7, Jul. '92/XXXVIII.
"Hormonal Manipulation of Meningiomas in vitro", Jeffrey J> Olson et al.
"Protection Against Oxidative Stress-induced Neuronal Cell Death—A Novel Role for RU486", Christian Behl et al., European Journal of Neuroscience, vol. 9, pp. 912-920, 1997.
"Auxiliary Therapeutic Use in Cancer and Related Disorders", Koide JRM, The Journal of Reproductive Medicine, vol. 43, No. 7, Jul. 1998.
"The Progesterone Antagonist", Arch Fam Med./vol. 2, Jan. 1993.
"Successful mifepristone treatment of recurrent, inoperable meningioma",The Lancet, p. 124-125, vol. 336, 1990.
"Mifepristone (RU 486)", R. M. Bonelli, Nr. 6/7, Juli '92/XXXVIII, 1992.
"Hormonal Manipulation of Meningiomas in vitro", Jeffrey J>Olson et al, 1996.
"Selective Activation of the Glucocorticoid Receptor by Steroid Antagonists in Human Breast Cancer and Osteosarcoma Cells", Christy J. Fryer et al., The Journal of Biological Chemistry, vol. 275, No. 23, Issue of Jun. 9, pp. 17771-17777, 2000.
"Protection Against Oxidative Stress-induced Neuronal Cell Death-A Novel Role for RU486", Christian Behl et al., European Journal of Neuroscience, vol. 9, pp. 912-920, 1997.
"Slowing the Progression of Cognitive Decline in Alzheimer's Disease Using Mifepristone," Joseph K. Belanoff et al., Journal of Molecular Neuoscience, vol. 19, 2002.
"RU-486 (Mifepristone) ameliorates diabetes but does not correct deficient β-adrenergic signalling in adipocytes from mature C57BL/6J-ob/ob mice," T.W. Gettys et al., International Journal of Obesity (1997) 21, 865-873.

* cited by examiner

*Primary Examiner* — Marcos Sznaidman
(74) *Attorney, Agent, or Firm* — Morgan, Lewis & Bockius LLP

(57) ABSTRACT

The invention relates to a novel use of compounds having formula (I), including mifepristone (RU 486 or RU 38 486) and the derivative salts thereof, for the preparation of a medicament that can modulate (activate or inhibit) the Hedgehog protein signalling pathway, which is intended for the treatment of pathologies involving a tissue dysfunction linked to deregulation of said pathway.

11 Claims, 1 Drawing Sheet

Figure 1:
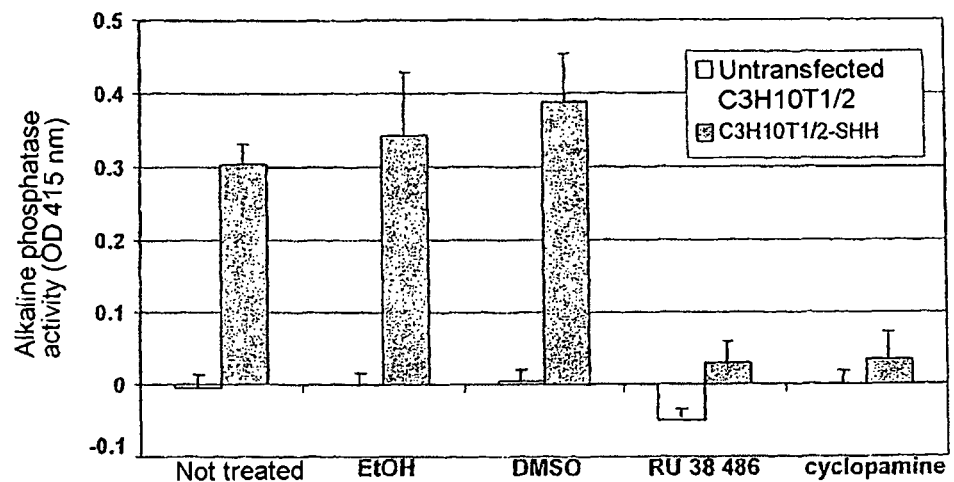

USE OF MIFEPRISTONE AND DERIVATIVES THEREFOR AS HEDGEHOG PROTEIN SIGNALING PATHWAY MODULATORS AND APPLICATIONS OF SAME

The present invention relates to a novel use of mifepristone and derivatives thereof as Hedgehog protein signaling pathway modulators, and also to applications thereof for the treatment of pathologies involving a tissue dysfunction associated with deregulation of this pathway.

The Hedgehog protein signaling pathway plays an essential role in the development of many embryonic tissues, in particular in the nervous system, and is thought to be involved in tissue maintenance and repair in adults.

The Hedgehog gene (Hh), which was isolated in drosophila and then in vertebrates, encodes a family of secreted and very conserved signaling proteins, the Hedgehog (Hh) proteins, which act as morphogens in many tissues (for a review, see: Ingham et al., Genes Dev., 2001, 15, 3059-3087; Marti et al., Trends Neurosci, 2002, 25, 89-96; Weschler et al., Annu Rev Neurosci, 2001, 24, 385-428). The Hh proteins are synthesized in the form of immature precursors of approximately 45 kDa that are autoprocessed into an active amino-terminal form (HhNp for N-terminal processed domain), which is doubly modified by the addition of two lipids: a cholesterol residue (carboxy-terminal ester linkage) and a palmitate (amino-terminal amide linkage). In mammals, three families of Hh proteins exist: Sonic (Shh), Indian (Ihh) and Desert (Dhh). Shh promotes ventralization of the neural tube, specifying the early phenotype of several types of neuron along the ventral median line (spinal cord motoneurons, dopaminergic or cholinergic neurons) and inducing the generation of oligodendrocyte precursors from the ventral spinal cord. Moreover, Shh induces gabaergic and dopaminergic neuron survival, directs the outcome of serotoninergic precursors and averts dopaminergic neuron death caused by the MPP toxin. Finally, it induces granular cell precursor proliferation in the early post-natal cerebellum. The other members of the Hedgehog family contribute, for their part, respectively to the development of bone tissue (Ihh), of the testes and of peripheral nerves (Dhh).

More recently, the Shh pathway has been identified in the adult brain, where the active amino-terminal form of the molecule is expressed in many regions of the mature nervous system, at a higher level than that encountered during the early post-natal period (Traiffort et al., Eur. J. Neurosci.: 1999: 11, 3199-3214 and 2001, 14, 839-850). Although the roles of Shh in adults have not been completely elucidated, it first emerged, like other neurotrophic molecules, as a factor capable of promoting the survival and maintenance of the phenotype of nervous system cells (Reilly et al., Mol. Cell. Neurosci., 2002, 19, 88-96; Charytoniuk et al., Eur. J. Neurosci., 2002, 16, 2351-2357). Under pathological conditions, such as a model of Parkinson's disease or a model of peripheral neuropathy, Shh is capable of preserving the axonal projections of dopaminergic neurons in the striatum or of improving the time required for motor recovery subsequent to crush of the sciatic nerve (Tsuboi et al., Exp. Neurol., 2002, 173, 95-104; Pepinski et al., J. Pharm. Sci., 2002, 91, 371-387).

The cellular response to the Hedgehog morphogen is controlled by the expression products of the Patched (Ptc) gene, which is a tumor suppressor gene, and of the Smoothened (Smo) proto-oncogene; however, the exact mechanism of regulation of the Hedgehog pathway has not been completely elucidated. In mammals, two Patched genes exist, encoding, respectively, Ptc1 and Ptc2, which are glycoproteins comprising 12 transmembrane domains, homologous to bacterial transporters. The product of the Smo gene, which encodes a protein of the G protein-coupled receptor family, has no known endogenous ligand. In the absence of Hedgehog, Ptc is thought to block the constitutive activity of Smo. The binding of Hedgehog to Ptc is thought to lift this inhibition and allow signal transduction via Smo. The mechanism of regulation of Smo activity by Ptc, in mammals, could involve a molecule that is transported by Ptc and that interacts with Smo (Taipale et al., Nature, 2002, 418, 892-896). Activation of the Gli transcription factors is involved in the cascade of events resulting from the activity of Smo. The type I transmembrane protein HIP (Hedgehog-Interacting Protein) constitutes another receptor for Hedgehog molecules, which it binds with an affinity comparable to that of Ptc; HIP has been proposed as a negative regulator of the pathway (Ingham et al., mentioned above; Ho et al., Curr. Opin. Neurobiol., 2002, 12, 57-63; Taipale et al., Nature, 2001, 411, 349-354). In addition, the products of the dispatched (disp) gene, in particular DispA, are thought to be involved in the release and accumulation in the extracellular medium of Hedgehog proteins in soluble form (Ma et al., Cell, 2002, 111, 63-75).

Dysfunctions of the Shh signaling pathway have been linked to many cancers, in particular subsequent to the characterization of Ptc as a tumor suppressor gene. Specifically, inactivating mutations of Ptc are linked to Gorlin syndrome or basal cell nevus syndrome, an autosomal dominant disease characterized by craniofacial and cerebral malformations, but especially by a high incidence of various tumors, more particularly basal cell carcinomas of the skin and medulloblastomas in the brain. Mice heterozygotes for the Ptc gene develop cerebellar tumors, suggesting that a modification of the Shh pathway is the cause of these tumors (Goodrich et al., Science, 1997, 277, 1109-1113).

Mutations in the human Ptc or Smo genes are also observed in primitive neuroectodermal tumors of the central nervous system, mainly medulloblastomas (30% of cases), but also in sporadic forms of basal cell carcinomas (40% and 20%, respectively, for Ptc and Smo). In addition, Shh mutations (H133Y) are also linked to basal cell carcinomas. The Smo mutations that involve mainly two amino acids in the seventh hydrophobic domain of the receptor (W535L and S533N) induce constitutive activation of the pathway, which escapes the negative control by Ptc. On the other hand, Ptc mutations result in a decrease in the inhibition that it exerts on Smo in the absence of Shh. In the two cases, activation of the Shh pathway results therefrom and leads to a powerful mitogenic activity demonstrated in cultures of developing cerebellar granular cell precursors, and to blocking of the terminal differentiation step of these neuroblasts (Traiffort et al., Eur. J.; Neurosci., 1999, mentioned above; Charytoniuk et al., J. Physiol. Paris, 2002, 96, 9-16; Dahmane et al., development, 1999, 126, 3089-3100; Wallace et al., Curr. Biol., 1999, 22, 103-114; Weshler-Reya et al., Neuron., 1999, 22, 103-114). Similarly, the expression of Smo carrying one of these mutations in transgenic mice results in the presence of basal cell carcinomas, which demonstrates the direct involvement of Smo in the development of these tumors (Xie et al., Nature, 1998, 391, 90-92).

Besides basal cell carcinomas and medulloblastomas, other types of tumors have been linked to a deficiency in the Hedgehog signaling pathway; the location of these tumors is tightly correlated with the sites of expression of the components of the pathway during embryonic development. By way of nonlimiting example, mention may be made of: breast cancers and meningiomas related to Ptc mutations, and glioblastomas related to Gli mutations.

Because of the essential role of the Hedgehog protein signaling pathway in many physiological processes and, consequently, of the importance of the pathologies linked to a dysfunction thereof, the components of this pathway, such as the Smoothened or Patched (Patched 1 and Patched 2) proteins, the Dispatched (Dispatched 1 and Dispatched 2) proteins or else the HIP protein, represent targets for the development of novel molecules capable of modulating (activating or inhibiting) this pathway and therefore of positively or negatively regulating the development [proliferation, differentiation, migration, survival (apoptosis)] and/or the activity of differentiated cells and of stem cells, in vitro and/or in vivo in the embryo or in the adult.

Such molecules are useful in the treatment of tumors related to hyperactivation of the Hedgehog pathway: nervous tissue tumors (medulloblastomas, primitive neuroectodermal tumors, glioblastomas, meningiomas and oligodendrogliomas), skin tumors (basal cell carcinomas, trichoepitheliomas), muscle and bone tissue tumors (rhabdomyosarcomas, osteosarcomas) and tumors of other tissues (kidney, bladder).

Such molecules are also useful in the treatment of neurodegenerative-type pathologies requiring blocking of the Hedgehog pathway (Parkinson's disease, Huntington's chorea, Alzheimer's disease, multiple sclerosis, motoneuron disease), and diseases in which blocking of the Hedgehog signaling pathway could be beneficial, such as diabetes.

Such molecules are also useful in the medical or surgical treatment (plastic or healing surgery, tissue or organ transplantation) of many acute, subacute or chronic, genetic or acquired pathologies—involving a tissue dysfunction linked to deregulation of the Hedgehog pathway—, for inducing the formation, the regeneration, the repair and/or an increase in the activity of tissues such as, without implied limitation: nervous tissue [central nervous system (brain) and peripheral nervous system (sensory, motor, sympathetic neurons)], bone, cartilage, testes, liver, spleen, intestine, pancreas, kidneys, smooth muscle and skeletal muscle, heart, lungs, skin and body hair system, mucous membranes, blood cells and cells of the immune system. By way of nonlimiting example of these pathologies, mention may in particular be made of neuropathies and related neuromuscular diseases, diabetes, alopecia, burns, ulcerations (skin and mucous membranes) and spermatogenesis disorders.

Various molecules capable of modulating the activity of the Hedgehog pathway have been identified:
- the Hedgehog proteins and derived polypeptides (fragments, variants, etc.), in particular Hedgehog protein agonists and antagonists (PCT international application WO 01/98344 in the name of Biogen); because of their size, these proteins and the derived polypeptides cannot cross the blood-brain barrier and cannot therefore be administered systemically, in particular for the treatment of brain tumors linked to hyperactivation of the Hedgehog protein signaling pathway. In addition, such molecules are difficult to produce and to purify and are relatively unstable;
- heterocyclic organic molecules (PCT international application WO 01/74344 in the name of Curis and Chen et al., PNAS, 2002, 99, 14071-14076);
- nitrogenous heterocyclic molecules (PCT international applications WO 01/19800, WO 01/26644 and WO 02/30421 in the name of Curis and Kamenetsky et al., J. Biol., 2002, 1, 1-19) and
- plant steroids derived from *Veratrum* spp (jervine, cyclopamine and cycloposine) and from *Solanum* spp. (solanidine), substituted in the 16-, 17- or 18-position with an amine or an amine derivative, and cholesterol:

U.S. Pat. No. 6,432,970 and PCT international applications WO 99/52534 and WO 01/27135 in the name of Johns Hopkins University School of Medicine; U.S. Pat. No. 6,291,516 and PCT international application WO 00/41545 in the name of Ontogeny and PCT international application WO 02/30462 in the name of Curis; Talpale et al., Nature, 2000, 406, 1005-1009; Berman et al., Science, 2002, 297, 1559-1561. However, cyclopamine is a teratogenic agent that causes holoprosencephaly and cyclopia in mammalian embryos, and an absence of toxicity, for mammals, has not been demonstrated for the other plant steroid-derived compounds.

It emerges from the above that no molecule currently exists that is effective for the treatment of pathological conditions requiring modulation of the activity of the Hedgehog protein signaling pathway, and for which a lack of toxicity has been verified by means of clinical trials in humans. Consequently, the inventors gave themselves the aim of providing compounds that better satisfy practical needs, in particular in that they are devoid of toxicity in humans and can therefore potentially be used in human therapy.

European patent EP 0 057 115 and U.S. Pat. No. 4,386,085 in the name of Roussel-Uclaf describe 19-nor steroid compounds substituted in the 11β-position. with a radical comprising a nitrogen, phosphorus or silicon atom, having anti-glucocorticoid, progestomimetic or anti-progestomimetic, androgenic or anti-androgenic properties. Because of these properties, the use of these steroid compounds is recommended for: combating conditions linked to hypersecretion of corticosteroids, especially for combating aging, in particular combating hypertension, atherosclerosis, diabetes, obesity and also immunodepression and insomnia, for preparing contraceptives, for combating hormone deregulation, especially hormone-dependent cancers, amenorrhea, dysmenorrhea and luteal insufficiency, and also for treating hypertrophies and cancer of the prostate, hyperandrogenism, anemia, hirsutism and acne.

Among these compounds, mifepristone (17β-hydroxy-11β-(4-dimethylaminophenyl)-17α-(prop-1-ynyl)estra-4,9-dien-3-one), also called RU-486 or RU-38486, is a 19-nor steroid substituted in the 11β-position with a radical comprising a nitrogen atom, which has a progesterone receptor antagonist activity and also a strong affinity for glucocorticoid receptors and a weak affinity for androgen receptors; this molecule has been given a marketing authorization for termination of pregnancy, and phase II clinical trials are ongoing for the treatment, in menopausal women, of metastatic breast cancers.

The inventors have shown that mifepristone and some of its derivatives, that differ from the abovementioned cyclopamine-derived steroids in that they do not have a primary, secondary or tertiary amine function, or nitrogenous heterocycle or amine derivatives substituted in the 16-, 17- and 18-position, are, surprisingly, active on the Hedgehog protein signaling pathway.

Because of its lack of toxicity in humans, mifepristone, which has been used in human therapy in various countries for many years, represents an advantageous alternative to cyclopamine and to its derivatives, for the treatment of pathological conditions requiring a modulation (activation or inhibition) of the activity of the Hedgehog protein signaling pathway.

Consequently, a subject of the present invention is the use of the compounds of formula (I)

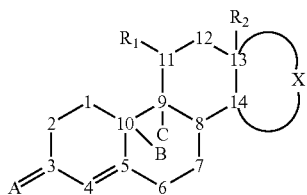

in which:
R$_1$ represents an organic radical containing from 1 to 18 carbon atoms, containing at least one nitrogen, phosphorus or silicon atom, the atom immediately adjacent to carbon 11 being a carbon atom,
R$_2$ represents a hydrocarbon-based radical containing from 1 to 8 carbon atoms,
X of formula:

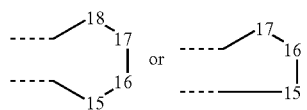

represents the residue of a saturated or unsaturated, pentagonal or hexagonal ring optionally substituted with one or more groups chosen from the following radicals: C$_1$-C$_{12}$ alkyl, alkenyl, alkynyl, aryl or aralkyl, hydroxyl —OH, carbonyl

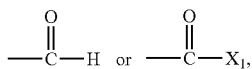

ether —O—X$_2$, ester

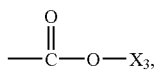

oxycarbonyl

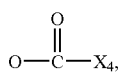

halogen, thiol, thioether —S—X$_5$, sulfinyl

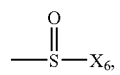

sulfonyl

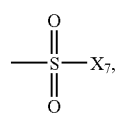

and also C$_1$-C$_{12}$ alkyl, alkenyl, alkynyl, aryl or aralkyl substituted with one or more hydroxyl —OH, carbonyl

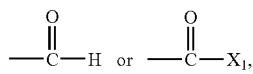

ether —O—X$_2$, ester

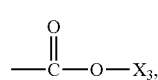

oxycarbonyl

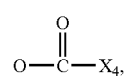

halogen, thiol, thioether —S—X$_5$, sulfinyl

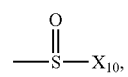

or sulfonyl

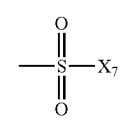

functions, with X$_1$, X$_2$, X$_3$, X$_4$, X$_5$, X$_6$ and X$_7$ representing C$_1$-C$_8$ alkyl, C$_2$-C$_8$ alkenyl or C$_2$-C$_8$ alkynyl groups, or C$_6$-C$_{15}$ aryl or C$_6$-C$_{15}$ aralkyl groups,
the group C=A in the 3-position represents an oxo group, which is free or blocked in the form of a ketal, an alcohol —CH—OH, ether —CH—O—Y$_1$, alkyl carboxylate

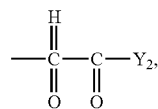

C=NOH or C=NO—Y$_3$ group, or a CH$_2$ group, Y$_1$, Y$_2$ and Y$_3$ representing an alkyl radical containing from 1 to 8 carbon atoms or an aralkyl group containing from 7 to 15 carbon atoms, and
B and C together form a double bond or an epoxide bridge, and of the derived salts, for preparing a medicinal product capable of modulating (activating or inhibiting) the Hedgehog protein signaling pathway, intended for the treatment of pathologies involving a tissue dysfunction linked to deregulation of this pathway.

Among the derived salts, mention may be made of the addition salts with acids of the compounds of formula I, for instance the salts formed with hydrochloric acid, hydrobromic acid, nitric acid, sulfuric acid, phosphoric acid, acetic acid, formic acid, propionic acid, benzoic acid, maleic acid, fumaric acid, succinic acid, tartaric acid, citric acid, oxalic acid, glyoxylic acid, aspartic acid, alkanesulfonic acids, such as methanesulfonic acid or ethanesulfonic acid, arylsulfonic acids, such as benzenesulfonic acid or para-toluenesulfonic acid, and arylcarboxylic acids.

According to an advantageous embodiment of the invention, $R_2$ represents a linear or branched, saturated alkyl radical containing from 1 to 4 carbon atoms, preferably a methyl radical.

According to another advantageous embodiment of the invention, X represents an optionally substituted pentagonal ring.

According to an advantageous arrangement of this embodiment, said pentagonal ring is substituted with at least one alkenyl or alkynyl group, preferably with an alkynyl group, preferably in the 17-position.

Advantageously, said pentagonal ring is also substituted with at least one hydroxyl group.

Preferably, X represents the residue of a pentagonal ring of formula:

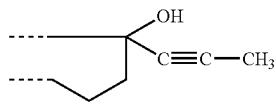

According to yet another advantageous embodiment of the invention, $R_1$ represents a hydrocarbon-based radical containing from 1 to 18 carbon atoms and containing at least one nitrogen atom, selected from:

the $R_1$ values which represent a primary, secondary or tertiary alkyl radical containing from 1 to 8 carbon atoms, in particular a methyl, ethyl, n-propyl, isopropyl, butyl, isobutyl, tert-butyl, pentyl, hexyl, cyclopropyl, cyclobutyl, cyclopentyl or cyclohexyl radical, containing at least one nitrogen atom or substituted with a heterocycle containing at least one nitrogen atom and optionally substituted with an alkyl radical containing from 1 to 8 carbon atoms, such as a methyl, ethyl or n-propyl radical, in particular 3,4- or 2-pyridyl radicals, the thiazolyl radical or the piperidinyl radical, and the $R_1$ values which represent an aryl or aralkyl radical carrying an amine function, in particular a phenyl or benzyl radical carrying an amine function:

in which $Z_1$ and $Z_2$, which may be identical or different, represent a linear, branched or cyclic alkyl radical containing from 1 to 8 carbon atoms, it being possible for $Z_1$ and $Z_2$ to be optionally combined so as to form a heterocycle with the nitrogen atom. Preferably, $Z_1$ and $Z_2$ represent a $C_1$-$C_4$ alkyl radical, and preferentially a methyl radical.

According to yet another advantageous embodiment of the invention, the group C=A in the 3-position represents an oxo group.

According to yet another advantageous embodiment of the invention, B and C together form a double bond.

According to an advantageous arrangement of the above embodiments, said compound of formula (I) is 17β-hydroxy-11β-(4-dimethylaminophenyl)-17α-(prop-1-ynyl)estra-4,9-dien-3-one of formula:

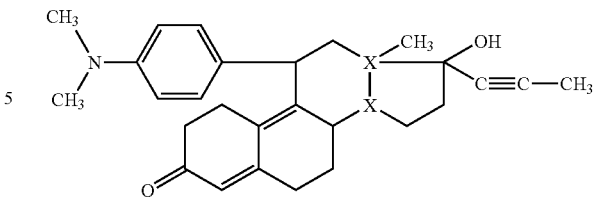

The compounds of formula I and their addition salts with pharmaceutically acceptable acids are produced as described in European patent 0 057 115 and U.S. Pat. No. 4,386,085.

The compounds of formula I and their addition salts with pharmaceutically acceptable acids which are capable of modulating the activity of the Hedgehog protein signaling pathway are used in the treatment of tumors linked to hyperactivation of the Hedgehog pathway, in particular nervous tissue tumors (medulloblastomas, primitive neuroectodermal tumors, glioblastomas, meningiomas and oligodendrogliomas), skin tumors (basal cell carcinomas, trichoepitheliomas), muscle and bone tissue tumors (rhabdomyosarcomas, osteosarcomas) and tumors of other tissues (kidney, bladder).

Such compounds are also used in the treatment of pathologies requiring blocking of the Hedgehog pathway, in particular neurodegenerative-type pathologies such as Parkinson's disease, Huntington's chorea, Alzheimer's disease, multiple sclerosis and motoneuron disease, or else other pathologies in which blocking of the Hedgehog signaling pathway could be beneficial, such as diabetes.

Such compounds are also used in the medical or surgical treatment (plastic or healing surgery, tissue or organ transplantation) of many acute, subacute or chronic, genetic or acquired pathologies involving a tissue dysfunction linked to deregulation of the Hedgehog pathway, for inducing, from stem cells or differentiated cells, the formation, the regeneration, the repair and/or an increase in the activity of tissues such as, without implied limitation: nervous tissue [central nervous system (brain) and peripheral nervous system (sensory, motor, sympathetic neurons)], bone, cartilage, testes, liver, spleen, intestine, pancreas, kidneys, smooth muscle and skeletal muscle, heart, lungs, skin and the body hair system, mucous membranes, blood cells and cells of the immune system. By way of nonlimiting example of these pathologies, mention may in particular be made of neuropathies and associated neuromuscular diseases, diabetes, alopecia, burns, ulcerations (skin and mucous membranes) and spermatogenesis disorders.

The useful dosage varies according to the condition to be treated, to the route and rate of administration, and also to the nature and the weight of the species to be treated (human or animal); it may, for example, vary from 100 mg to 1 g per day in adults, when administered orally.

The compounds of formula (I) and their salts are used via the digestive route (orally or sublingually), parenterally or locally. They may be in the form of simple or sugar-coated tablets, of gelatin capsules, of granules, of syrup, of suppositories, of injectable preparations, of ointments, of creams, of gels or of an aerosol, which are prepared according to the usual methods.

In these pharmaceutical forms, the compounds of formula (I) are incorporated into excipients conventionally used in pharmaceutical compositions, such as talc, gum arabic, lactose, starch, magnesium stearate, cocoa butter, aqueous or nonaqueous carriers, fatty substances of animal or plant origin, paraffin derivatives, glycols, various wetting agents, dispersants or emulsifiers, or preserving agents.

The use of the compounds of formula (I) as defined above, and in particular of mifepristone, is more advantageous than that of the existing Hedgehog protein signaling pathway modulators in that these compounds are devoid of toxicity in humans and can therefore effectively be used in human therapy, unlike cyclopamine and its derivatives, which are teratogenic.

Figure 2:
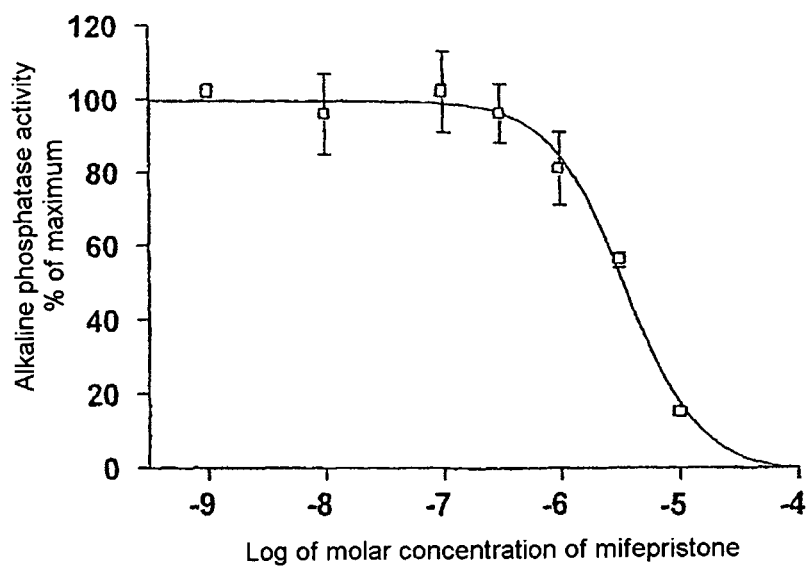

Besides the above arrangements, the invention also comprises other arrangements which will emerge from the following description, which refers to examples of use of mifepristone and of its derivatives according to the present invention, and also to the attached drawings in which:

FIG. 1 illustrates the inhibition, by mifepristone, of the differentiation of mesenchymal cells (C3H10T1/2 line) induced by the Sonic Hedgehog (Shh) protein. Untransfected C3H10T1/2 cells (white columns) and those transfected with the Shh protein expression plasmid, called pRK5 (C3H10T1/2-SHH, grayish columns), are treated for 5 days with mifepristone (RU 38 486, 10 µM), cyclopamine (10 µM) or their respective carriers, dimethyl sulfoxide (DMSO) or ethanol (EtOH), or are not treated. The differentiation of the C3H10T1/2 cells, which is accompanied by induction of alkaline phosphatase activity, is then evaluated by measuring the optical density at 415 nm, in the presence of the alkaline phosphatase substrate, para-nitrophenyl phosphate. The values indicated correspond to the mean±standard error (n=4), and FIG. 2 illustrates the dose-effect curve for the inhibition of differentiation of the C3H10T1/2 cells by mifepristone. C3H10T1/2 cells transfected with the Shh protein expression plasmid, called pRK5, are treated for 5 days with increasing amounts of mifepristone (RU 38 486, 1 nM to 10 µM) or are not treated. The inhibition of differentiation of the C3H10T1/2 cells is expressed through the percentage alkaline phosphatase activity, relative to the nontreated cells (maximum activity=100%). The values indicated correspond to the mean±standard error (n=4) of two independent experiments. The concentration that inhibits 50% of cell differentiation ($IC_{50}$) is 3.7 µM±0.3 µM.

EXAMPLE

Effect of Mifepristone on the Hedgehog Protein Signaling Pathway

The effect of mifepristone on the Hedgehog protein signaling pathway is determined by analyzing the differentiation of the C3H10T1/2 pluripotent fibroblast cell line, induced beforehand with the ShhN protein, in the presence or absence of mifepristone or of cyclopamine, for comparison.

1) Materials and methods

The C3H10T1/2 pluripotent fibroblast cell line (ATCC) is cultured under the conditions recommended by the ATCC. C3H10T1/2 cells were transfected with the plasmid pRK5 encoding the mouse Shh protein (Taipale et al., Nature, 2001, 411, 349-354), using calcium phosphate, according to conventional protocols. The cells were then cultured for 5 days in the presence of mifepristone (10 µM), of cyclopamine (10 µM) or else of corresponding volumes of their respective carriers, dimethyl sulfoxide (DMSO) and ethanol (EtOH); the alkaline phosphatase activity induced by the differentiation of the C3H10T1/2 cells into muscle, adipocyte, chondrocyte or osteoblast cells was then evaluated by measuring the optical density at 415 nm, in the presence of the alkaline phosphatase substrate, para-nitrophenyl phosphate. Alternatively, the dose-response curve for mifepristone was determined under the same experimental conditions, in the presence of increasing concentrations of mifepristone (1 nM to 10 µM).

2) Results a) Comparative Effect of Mifepristone and of Cyclopamine on C3H10T1/2 Cell Differentiation The results given in FIG. 1 show that the 3- to 10-fold increase in alkaline phosphatase activity that is induced by the overexpression of Shh is completely inhibited in the presence of 10 µM of mifepristone or of cyclopamine.

These results demonstrate that mifepristone, which, unlike cyclopamine, is devoid of any teratogenic effect, is capable, like cyclopamine, of blocking the Shh protein-induced differentiation of mesenchymal cells. Mifepristone therefore represents a Hedgehog protein signaling pathway antagonist that is devoid of any teratogenic effect and that is useful for the treatment of pathologies requiring blocking of the Hedgehog pathway, such as cancer, neurodegenerative diseases and diabetes.

b) Dose-Effect Curve for the Inhibition of C3H10T1/2 Cell Differentiation by Mifepristone The results given in FIG. 2, which confirm those given in FIG. 1, show that a concentration of 10 µM of mifepristone completely inhibits the activation of alkaline phosphatase induced by the overexpression of the Shh protein. The concentration that inhibits 50% of cell differentiation ($IC_{50}$) is 3.7 µM±0.3 µM.

As emerges from the above, the invention is in no way limited to its methods of implementation, execution and application which have just been described more explicitly; on the contrary, it encompasses all the variants thereof which may occur to those skilled in the art, without departing from the context or the scope of the present invention.

The invention claimed is:

1. A method of treating tumors in a mammal, which comprises administering to the mammal an amount of 17[beta]-hydroxy-11[beta]-(4-dimethylaminophenyl)-17[alpha]-(prop-1-ynyl)estra-4,9-dien-3-one of the formula:

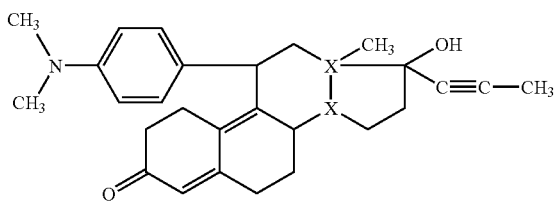

or an acid addition salt thereof effective to treat tumors linked to hyperactivation of the Hedgehog pathway, wherein the tumors are selected from the group consisting of medulloblastomas, oligodendrogliomas, basal cell carcinomas, trichoepitheliomas, rhabdomyosarcomas, and tumors of kidney.

2. The method of claim 1, wherein said effective amount of 17[beta]-hydroxy-11[beta]-(4-dimethylaminophenyl)-17[alpha]-(prop-1-ynyl)estra-4,9-dien-3-one is administered orally or sublingually.

3. The method of claim 1, wherein said effective amount of 17[beta]-hydroxy-11[beta]-(4-dimethylaminophenyl)-17[alpha]-(prop-1-ynyl)estra-4,9-dien-3-one is administered parenterally.

4. The method of claim 1, wherein said effective amount of 17[beta]-hydroxy-11[beta]-(4-dimethylaminophenyl)-17[alpha]-(prop-1-ynyl)estra-4,9-dien-3-one is administered locally.

5. The method of claim 1, wherein an acid addition salt is administered.

6. The method of claim 5, wherein the acid addition salt is a salt of an inorganic acid.

7. The method of claim 5, wherein the acid addition salt is a salt of an organic acid.

8. The method of claim 2, wherein said effective amount administered is from 100 mg to 1 g per day for an adult human.

9. The method of claim 6, wherein the inorganic acid addition salt is a salt of hydrochloric acid, hydrobromic acid, nitric acid, sulfuric acid or phosphoric acid.

10. The method of claim 7, wherein the organic acid addition salt is a salt of acetic acid, benzoic acid, maleic acid, fumaric acid, succinic acid, tartaric acid, citric acid or aspartic acid.

11. The method of claim 1, wherein the mammal is a human.

\* \* \* \* \*